United States Patent [19]

O'Brien et al.

[11] Patent Number: 5,811,634
[45] Date of Patent: Sep. 22, 1998

[54] TRANSGENIC MAMMAL ENCODING ORNITHINE DECARBOXYLASE

[75] Inventors: Thomas G. O'Brien, 1209 Childs Ave., Drexel Hill, Pa. 19026; Janet A. Sawicki, 4 Aspen Ct., Newtown Square, Pa. 19073; Susan K. Gilmour, Wynnewood; Louis C. Megosh, Upper Darby, both of Pa.; Manfred Blessing, Neupforte, Apt 19, Saulheim, Germany, 55291

[73] Assignees: Thomas G. O'Brien, Drexil Hill; Janet A. Sawicki, Newtown Square; Louis Megosh, Upper Darby; Dan Rosson; Susan Gilmour, both of Wynnewood, all of Pa.; Manfred Blessing, Saulheim, Germany

[21] Appl. No.: 527,227

[22] Filed: Sep. 12, 1995

[51] Int. Cl.$^6$ .......................... A61K 48/00; C12N 15/63; C12N 15/79
[52] U.S. Cl. .................. 800/2; 435/320.1; 435/172.3; 435/69.1; 435/375; 935/62; 935/34; 935/70; 424/9.1
[58] Field of Search .............................. 800/2; 435/320.1, 435/7.2, 6, 69.1, 172.3; 424/9.1

[56] References Cited

FOREIGN PATENT DOCUMENTS 0633315   3/1994   European Pat. Off. .

OTHER PUBLICATIONS

O'Brien et al., "Induction of the Polyamine–Biosynthetic Enzymes in Mouse Epidermis by Tumor–Promoting Agents", *Cancer Research* (1975), 35:1662–1670.

Metcalf et al., "Catalytic Irreversible Inhibition of Mammalian Ornithine Decarboxylase (E.C. 4.1.1.17) by Substrate and Product Analogues", *J. Am. Chem. Soc.* (1978), 100(8):2551–2553.

Weeks et al., "α–Difluoromethylornithine, an Irreversible Inhibitor of Ornithine Decarboxylase, Inhibits Tumor Promoter–Induced Polyamine Accumulation and Carcinogenesis in Mouse Skin", *Proc. Natl. Acad. Sci. USA* (1982) 79:6028–6032.

Seely et al., "Changes in Mouse Kidney Ornithine Decarboxylase Activity are Brought About by Changes in the Amount of Enzyme Protein as Measured by Radioimmunoassay", *J. Biol. Chem.* (1983), 258(4):2496–2500.

Jorcano et al., "Amino Acid Sequence Diversity Between Bovine Epidermal Cytokeratin Polypeptides of the Basic (Type II) Subfamily as Determined from cDNA Clones", *Differentiation* (1984), 28:155–163.

Gupta et al., "Mouse Ornithine Decarboxylase (Complete Amino Acid Sequence Deduced from cDNA)", *J. Biol. Chem.* (1985), 260(5):2941–2944.

Gilmour et al., "Heterogeneity of Orinithine Decarboxylase Expression in 12–O–tetradecanolyphorbol–13–Acetate–Treated Mouse Skin and in Epidermal Tumors", *Carcinogenesis* (1986), 7(6):943–947.

Palmiter et al., "Germ–Line Transformation of Mice", *Ann. Rev. Genet.* (1986), 20:465–499.

Blessing et al., "Differentially Expressed Bovine Cytokeratin Genes. Analysis of Gene Linkage and Evolutionary Conservation of 5'–Upstream Sequences" (1987), *EMBO Journal* 6(3):567–575.

Pegg, "Polyamine Metabolism and Its Importance in Neoplastic Growth and as a Target for Chemotherapy", *Cancer Res.* (1988), 48:759–774.

Blessing et al., "Enhancer Elements Directing Cell–Type–Specific Expression of Cytokeratin Genes and Changes of the Epithelial Cytoskeleton by Transfections of Hybrid Cytokeratin Genes", (1989), *EMBO Journal* 8(1): 117–126.

Ghoda et al., "Prevention of Rapid Intracellular Degradation of ODC by a Carboxyl–Terminal Truncation", *Science* (1989), 243:1493–1495.

Jorcano et al., "Identification of Two Types of Keratin Polypeptides Within the Acidic Cytokeratin Subfamily I", *J. Mol. Biol.* (1989), 179:257–281.

Bailleul et al., "Skin Hyperkeratosis and Papilloma Formation in Transgenic Mice Expressing a ras Oncogene from a Suprabasal Keratin Promoter" (1990), *Cell* 62:697–708.

Rothnagel et al., "Development of an Epidermal–Specific Expression Vector for targeting Gene Expression to the Epidermis of Transgenic Mice", *ABSTRACTS (J. Invest. Dermatol.)* (1990), 94(4):573.

Halmekytö et al., "Characterization of a Transgenic Mouse Line Over–Expressing the Human Ornithine Decarboxylase Gene" (1991), *Biochem. J.* 278:895–989.

Halmekytö et al., "Trangenic Mice Aberrantly Expressing Human Ornithine Decarboxylase Gene", (1991) *J. Biol. Chem* 266(29):19746–19751.

Hibshoosh et al., "Effects of Overexpression of Ornithine Decarboxylase (ODC) on Growth Control and Oncogene–Induced Cell Transformation", *Oncogene* (1991), 6:739–743.

Koza et al., "Constitutively Elevated Levels of Ornithine and Polyamines in Mouse Epidermal Papillomas", *Carcinogenesis* (1991), 12(9):1619–1625.

Halmekytö et al., "Enhanced Papilloma Formation in Response to Skin Tumor Promotion in Transgenic Mice Overexpressing the Human Ornithine Decarboxylase Gene", (1992), *Biochem. and Biophys. Res. Comm.* 187(1):493–497.

(List continued on next page.)

Primary Examiner—Jasemine C. Chambers
Assistant Examiner—Karen M. Hauda
Attorney, Agent, or Firm—Panitch Schwarz Jacobs & Nadel, P.C.

[57] ABSTRACT

The invention features a transgenic mammal encoding a chimeric ornithine decarboxylase gene, which transgenic mammal exhibits phenotypic abnormalities. The invention also includes a chimeric transgene comprising ornithine decarboxylase.

23 Claims, 11 Drawing Sheets
(1 of 11 Drawing(s) Filed in Color)

OTHER PUBLICATIONS

Kauppinen et al., "Nuclear Magnetic Resonance Spectroscopy Study on Energy Metabolism, Intracellular pH, and Free $Mg^{2+}$ Concentration in the Brain of Transgenic Mice Overexpressing Human Ornithine Decarboxylase Gene" (1992) *J. Neurochem.* 58(3):831–836.

Blessing et al., "Transgenic Mice as a Model to Study the Role of TGF-β–Related Molecules in Hair Follicles" (1993), *Genes& Development* 7:204–215.

Greenhalgh et al., "Hyperplasia, Hyperkeratosis and benign Tumor Production in Transgenic Mice by a Targeted v–fos Oncogene Suggest a Role for fos in Epidermal Differentiation and Neoplasia" (1993), *Oncogene* 8: 2145–2157.

Hakovirta et al., "Polyamines and Regulation of Spermatogenesis: Selective Stimulation of Late Spermatogonia in Transgenic Mice Overexpressing the Human Ornithine Decarboxylase Gene," (1993), *Mol. Endocrinol.* 7(11): 1430–1436.

Halmekytö et al., "Regulation of the Expression of Human Ornithine Decarboxylase Gene and Ornithine Decarboxylase Promoter–Driven Reporter Gene in Transgenic Mice" (1993), *Biochem. J.* 292:927–932.

Halmekytö et al., "Transgenic Mice Over–Producing Putrescine in Their Tissues do not Convert the diamine into Higher Polyamines" (1993), *Biochem. J.* 291:505–508.

Halonen et al., "Elevated Seizure Threshold and Impaired Spatial Learning in Transgenic Mice with Putrescine Overproduction in the Brain" (1993), *Eur. J. Neuroscience* 5: 1333–1239.

Blessing et al., "Chemical skin Carcinogenesis is Prevented in Mice by the Induced Expression of a TFG-β Related Transgene" (1995), *Teratogenesis, Carcinogenesis, and Mutagenesis* 15:11–21.

Ramirez et al., "A 5'–Upstream Region of a Bovine Keratin 6 Gene Confers Tissue–Specific Expression and Hyperproliferation–Related Induction in Transgenic Mice" (1995), *Proc. Natl. Acad. Sci. USA* 92:4783–4787.

Megosh et al., "Increased Frequency of Spontaneous Skin Tumors in Transgenic Mice which Overexpress Ornithine Decarboxylase" (1995) *Cancer Research* 55:4205–4209.

O'Brien et al., "Transgenic Mice Overexpressing Ornithine Decarboxylase (ODC) in Epidermis" (1995) AACR (*American Asociation for Cancer Research, Inc.*) Abstract Form, one page.

Kappel et al. "Regulating gene expression in transgenic animals," Current Opinion in Biotechnology, vol. 3: 548–553, 1992.

Strojek et al. "The use of trangenic animal techniques for livestock improvement," Genetic Engineering: Principles and Methods, vol. 10: 227–246, 1988.

Houdebine, L. "Production of pharmaceutical proteins from transgenic animals," J. of biotechnology, vol. 34: 269–287, 1994.

Wall, R.J. "Transgenic Livestock: Progress and Prospects for the Future," Theriogenology, vol. 45: 57–68, 1996.

Searle et al. "Stomach cancer in transgenic mice expressing human papillomavirus type 16 early region genes from a keratin promoter," J. of General Virology, vol. 75: 1125–1137, 1994.

Keough et al. "Targeted expression of SV40 T–antigen in the hair follicle of transgenic mice produces aberrant hair phenotype," J. of Cell Science, vol. 108: 957–966, Mar. 1995.

Guo et al. "Targeting expression of keratinocyte growth factor to keratinocytes elicits striking changes in epithelial differentiation in transgenic mice," The EMBO J., vol. 12(3): 973–986, 1993.

```
              10          20          30          40
    *    *    *    *    *    *    *    *    *
   AAG  CTT  GTT  CTT  ATG  CTG  TAA  AAA  CTC  ATC  TCC  TTT  GTC  CCT  CTT
         50             60             70             80             90
         *    *    *    *    *    *    *    *    *
   GCC  TTT  CAA  AGG  AGT  GTC  ATG  TCC  CCA  GAG  TAG  CCC  CCA  ATT  CCC
             100            110            120            130
    *    *    *    *    *    *    *    *    *
   AGG  CCA  GGC  CAC  CAG  GAA  GGC  AGT  CAG  GAG  ATC  CAG  AAG  GAC  ATG
         140            150            160            170            180
         *    *    *    *    *    *    *    *    *
   TTC  AAA  CAT  GGC  CCA  AAA  CCA  CCG  CAA  GCC  ACT  TTC  TTG  CTC  AGA
             190            200            210            220
    *    *    *    *    *    *    *    *    *
   CCA  CAG  GCA  AAT  GCC  TAT  TAA  CCC  TCA  GAG  ACG  TTC  AAC  CTG  AAT
         230            240            250            260            270
         *    *    *    *    *    *    *    *    *
   GGG  AAG  GGT  GGT  GTG  AGT  GGA  GAA  GAA  AAC  TTG  TGT  GGG  AAG  GGG
             280            290            300            310
    *    *    *    *    *    *    *    *    *
   GCA  AGA  GAA  GAG  TGT  CTG  AGT  AAG  CAG  AAG  GAG  GGA  ACA  ATT  ATC
         320            330            340            350            360
         *    *    *    *    *    *    *    *    *
   ACA  GAT  CAG  CTC  CTT  GTC  TCC  TTT  GTT  TGA  GAG  CAT  GAC  TAA  CCC
             370            380            390            400
    *    *    *    *    *    *    *    *    *
   ATG  ACT  TCA  GTG  AAT  TTA  CAT  CCA  GTG  GTA  TTG  TGT  TGG  GAT  CAA
         410            420            430            440            450
         *    *    *    *    *    *    *    *    *
   GTC  AAG  GCT  AGA  AGC  CAG  AAG  AAT  TTC  TCC  ATG  ACT  AAA  GGA  AAC
             460            470            480            490
    *    *    *    *    *    *    *    *    *
   CAA  AGA  AGC  AAT  ATT  CAT  ACT  TCA  TAC  CTT  TCT  AGA  GGC  AGG  GGG
         500            510            520            530            540
         *    *    *    *    *    *    *    *    *
   TGA  TCT  CAC  TAT  TTG  TAA  AGC  CCA  GCC  CTT  TCT  AAT  CTG  CAG  GCT
             550            560            570            580
    *    *    *    *    *    *    *    *    *
   CAC  CTT  CCA  GGA  CTG  AGC  CCG  GCC  CAT  TTT  TCA  CAT  ATA  TAA  GCT
         590            600            610            620            630
         *    *    *    *    *    *    *    *    *
   GCT  GCC  GGG  CCG  CCC  TCT  ATA  GAT  CTG  GAT  CTC  GAC  GGT  ATC  GAT
```

```
             10            20            30            40
         *    *    *    *    *    *    *    *    *
        GTC  GAC  CTT  GTG  AGG  AGC  TGG  TGA  TAA  TTT  GAT  TCC  ATC  TCC  AGG
             50            60            70            80            90
         *    *    *    *    *    *    *    *    *
        TTC  CCT  GTA  AGC  ACA  TCG  AGA  ACC  ATG  AGC  AGC  TTT  ACT  AAG  GAC
                                               Met  Ser  Ser  Phe  Thr  Lys  Asp>
                                                    ___ORNITHINE DECARBOXYL____>
                  100           110           120           130
         *    *    *    *    *    *    *    *    *
        GAG  TTT  GAC  TGC  CAC  ATC  CTT  GAT  GAA  GGC  TTT  ACT  GCT  AAG  GAC
        Glu  Phe  Asp  Cys  His  Ile  Leu  Asp  Glu  Gly  Phe  Thr  Ala  Lys  Asp>
        ___a___a____ORNITHINE DECARBOXYLASE. 4.1.1.17__a___a___a___>
             140           150           160           170           180
         *    *    *    *    *    *    *    *    *
        ATT  CTG  GAC  CAA  AAA  ATC  AAT  GAA  GTC  TCT  TCC  TCT  GAC  GAT  AAG
        Ile  Leu  Asp  Gln  Lys  Ile  Asn  Glu  Val  Ser  Ser  Ser  Asp  Asp  Lys>
        ___a___a____ORNITHINE DECARBOXYLASE. 4.1.1.17__a___a___a___>
                  190           200           210           220
         *    *    *    *    *    *    *    *    *
        GAT  GCG  TTC  TAT  GTT  GCG  GAC  CTC  GGA  GAC  ATT  CTA  AAG  AAG  CAT
        Asp  Ala  Phe  Tyr  Val  Ala  Asp  Leu  Gly  Asp  Ile  Leu  Lys  Lys  His>
        ___a___a____ORNITHINE DECARBOXYLASE. 4.1.1.17__a___a___a___>
             230           240           250           260           270
         *    *    *    *    *    *    *    *    *
        CTG  AGG  TGG  CTA  AAA  GCT  CTT  CCC  CGC  GTC  ACT  CCC  TTT  TAC  GCA
        Leu  Arg  Trp  Leu  Lys  Ala  Leu  Pro  Arg  Val  Thr  Pro  Phe  Tyr  Ala>
        ___a___a____ORNITHINE DECARBOXYLASE. 4.1.1.17__a___a___a___>
                  280           290           300           310
         *    *    *    *    *    *    *    *    *
        GTC  AAG  TGT  AAC  GAT  AGC  AGA  GCC  ATA  GTG  AGC  ACC  CTA  GCT  GCC
        Val  Lys  Cys  Asn  Asp  Ser  Arg  Ala  Ile  Val  Ser  Thr  Leu  Ala  Ala>
        ___a___a____ORNITHINE DECARBOXYLASE. 4.1.1.17__a___a___a___>
             320           330           340           350           360
         *    *    *    *    *    *    *    *    *
        ATT  GGG  ACA  GGA  TTT  GAC  TGT  GCA  AGC  AAG  ACT  GAA  ATA  CAG  TTG
        Ile  Gly  Thr  Gly  Phe  Asp  Cys  Ala  Ser  Lys  Thr  Glu  Ile  Gln  Leu>
        ___a___a____ORNITHINE DECARBOXYLASE. 4.1.1.17__a___a___a___>
                  370           380           390           400
         *    *    *    *    *    *    *    *    *
        GTG  CAG  GGG  CTT  GGG  GTG  CCT  GCA  GAG  AGG  GTT  ATC  TAT  GCA  AAT
        Val  Gln  Gly  Leu  Gly  Val  Pro  Ala  Glu  Arg  Val  Ile  Tyr  Ala  Asn>
        ___a___a____ORNITHINE DECARBOXYLASE. 4.1.1.17__a___a___a___>
             410           420           430           440           450
         *    *    *    *    *    *    *    *    *
        CCT  TGT  AAG  CAA  GTC  TCT  CAA  ATC  AAG  TAT  GCT  GCC  AGT  AAC  GGA
        Pro  Cys  Lys  Gln  Val  Ser  Gln  Ile  Lys  Tyr  Ala  Ala  Ser  Asn  Gly>
        ___a___a____ORNITHINE DECARBOXYLASE. 4.1.1.17__a___a___a___>
```

FIG. 2B

```
         460          470          480          490
          *    *      *    *      *    *      *    *      *
        GTC  CAG  ATG  ATG  ACT  TTT  GAC  AGT  GAA  ATT  GAA  TTG  ATG  AAA  GTC
        Val  Gln  Met  Met  Thr  Phe  Asp  Ser  Glu  Ile  Glu  Leu  Met  Lys  Val>
        ___a___a____ORNITHINE DECARBOXYLASE. 4.1.1.17__a___a___a___>
         500          510          520          530          540
          *    *      *    *      *    *      *    *      *
        GCC  AGA  GCA  CAT  CCA  AAG  GCA  AAG  TTG  GTT  CTA  CGG  ATT  GCC  ACT
        Ala  Arg  Ala  His  Pro  Lys  Ala  Lys  Leu  Val  Leu  Arg  Ile  Ala  Thr>
        ___a___a____ORNITHINE DECARBOXYLASE. 4.1.1.17__a___a___a___>
         550          560          570          580
          *    *      *    *      *    *      *    *      *
        GAT  GAT  TCC  AAA  GCT  GTC  TGT  CGC  CTC  AGT  GTT  AAG  TTT  GGT  GCC
        Asp  Asp  Ser  Lys  Ala  Val  Cys  Arg  Leu  Ser  Val  Lys  Phe  Gly  Ala>
        ___a___a____ORNITHINE DECARBOXYLASE. 4.1.1.17__a___a___a___>
         590          600          610          620          630
          *    *      *    *      *    *      *    *      *
        ACA  CTC  AAA  ACC  AGC  AGG  CTT  CTC  TTG  GAA  CGG  GCA  AAA  GAG  CTA
        Thr  Leu  Lys  Thr  Ser  Arg  Leu  Leu  Leu  Glu  Arg  Ala  Lys  Glu  Leu>
        ___a___a____ORNITHINE DECARBOXYLASE. 4.1.1.17__a___a___a___>
         640          650          660          670
          *    *      *    *      *    *      *    *      *
        AAT  ATT  GAC  GTC  ATT  GGT  GTG  AGC  TTC  CAT  GTG  GGC  AGT  GGA  TGT
        Asn  Ile  Asp  Val  Ile  Gly  Val  Ser  Phe  His  Val  Gly  Ser  Gly  Cys>
        ___a___a____ORNITHINE DECARBOXYLASE. 4.1.1.17__a___a___a___>
         680          690          700          710          720
          *    *      *    *      *    *      *    *      *
        ACT  GAT  CCT  GAT  ACC  TTC  GTT  CAG  GCA  GTG  TCG  GAT  GCC  CGC  TGT
        Thr  Asp  Pro  Asp  Thr  Phe  Val  Gln  Ala  Val  Ser  Asp  Ala  Arg  Cys>
        ___a___a____ORNITHINE DECARBOXYLASE. 4.1.1.17__a___a___a___>
         730          740          750          760
          *    *      *    *      *    *      *    *      *
        GTG  TTT  GAC  ATG  GCA  ACA  GAA  GTT  GGT  TTC  AGC  ATG  CAT  CTG  CTT
        Val  Phe  Asp  Met  Ala  Thr  Glu  Val  Gly  Phe  Ser  Met  His  Leu  Leu>
        ___a___a____ORNITHINE DECARBOXYLASE. 4.1.1.17__a___a___a___>
         770          780          790          800          810
          *    *      *    *      *    *      *    *      *
        GAT  ATT  GGT  GGT  GGC  TTT  CCT  GGA  TCT  GAA  GAT  ACA  AAG  CTT  AAA
        Asp  Ile  Gly  Gly  Gly  Phe  Pro  Gly  Ser  Glu  Asp  Thr  Lys  Leu  Lys>
        ___a___a____ORNITHINE DECARBOXYLASE. 4.1.1.17__a___a___a___>
         820          830          840          850
          *    *      *    *      *    *      *    *      *
        TTT  GAA  GAG  ATC  ACC  AGT  GTA  ATC  AAC  CCA  GCT  CTG  GAC  AAG  TAC
        Phe  Glu  Glu  Ile  Thr  Ser  Val  Ile  Asn  Pro  Ala  Leu  Asp  Lys  Tyr>
        ___a___a____ORNITHINE DECARBOXYLASE. 4.1.1.17__a___a___a___>
```

FIG. 2C

```
        860         870         880         890         900
         *     *     *     *     *     *     *     *     *
TTC CCA TCA GAC TCT GGA GTG AGA ATC ATA GCT GAG CCA GGC AGA
Phe Pro Ser Asp Ser Gly Val Arg Ile Ile Ala Glu Pro Gly Arg>
___a___a____ORNITHINE DECARBOXYLASE. 4.1.1.17__a___a___a___>
              910         920         930         940
               *     *     *     *     *     *     *     *     *
TAC TAT GTC GCA TCA GCT TTC ACG CTT GCA GTC AAC ATC ATT GCC
Tyr Tyr Val Ala Ser Ala Phe Thr Leu Ala Val Asn Ile Ile Ala>
___a___a____ORNITHINE DECARBOXYLASE. 4.1.1.17__a___a___a___>
        950         960         970         980         990
         *     *     *     *     *     *     *     *     *
AAA AAA ACC GTG TGG AAG GAG CAG CCC GGC TCT GAC GAT GAA GAT
Lys Lys Thr Val Trp Lys Glu Gln Pro Gly Ser Asp Asp Glu Asp>
___a___a____ORNITHINE DECARBOXYLASE. 4.1.1.17__a___a___a___>
             1000        1010        1020        1030
               *     *     *     *     *     *     *     *     *
GAG TCA AAT GAA CAA ACC TTC ATG TAT TAT GTG AAT GAT GGA GTA
Glu Ser Asn Glu Gln Thr Phe Met Tyr Tyr Val Asn Asp Gly Val>
___a___a____ORNITHINE DECARBOXYLASE. 4.1.1.17__a___a___a___>
       1040        1050        1060        1070        1080
         *     *     *     *     *     *     *     *     *
TAT GGA TCA TTT AAC TGC ATT CTT TAT GAT CAT GCC CAT GTG AAG
Tyr Gly Ser Phe Asn Cys Ile Leu Tyr Asp His Ala His Val Lys>
___a___a____ORNITHINE DECARBOXYLASE. 4.1.1.17__a___a___a___>
             1090        1100        1110        1120
               *     *     *     *     *     *     *     *     *
GCC CTG CTG CAG AAG AGA CCC AAG CCA GAC GAG AAG TAT TAC TCA
Ala Leu Leu Gln Lys Arg Pro Lys Pro Asp Glu Lys Tyr Tyr Ser>
___a___a____ORNITHINE DECARBOXYLASE. 4.1.1.17__a___a___a___>
       1130        1140        1150        1160        1170
         *     *     *     *     *     *     *     *     *
TCC AGC ATC TGG GGA CCA ACA TGT GAT GGC CTT GAT CGG ATC GTG
Ser Ser Ile Trp Gly Pro Thr Cys Asp Gly Leu Asp Arg Ile Val>
___a___a____ORNITHINE DECARBOXYLASE. 4.1.1.17__a___a___a___>
             1180        1190        1200        1210
               *     *     *     *     *     *     *     *     *
GAG CGC TGT AAC CTG CCT GAA ATG CAT GTG GGT GAT TGG ATG CTG
Glu Arg Cys Asn Leu Pro Glu Met His Val Gly Asp Trp Met Leu>
___a___a____ORNITHINE DECARBOXYLASE. 4.1.1.17__a___a___a___>
       1220        1230        1240        1250        1260
         *     *     *     *     *     *     *     *     *
TTT GAG AAC ATG GGT GCA TAC ACC GTT GCT GCT GCT TCT ACT TTC
Phe Glu Asn Met Gly Ala Tyr Thr Val Ala Ala Ala Ser Thr Phe>
___a___a____ORNITHINE DECARBOXYLASE. 4.1.1.17__a___a___a___>
```

FIG. 2D

```
        1270          1280          1290          1300
          *       *     *       *     *       *     *       *     *
AAT GGG TTC CAG AGG CCA AAC ATC TAC TAT GTA ATG TCA CGG CCA
Asn Gly Phe Gln Arg Pro Asn Ile Tyr Tyr Val Met Ser Arg Pro>
___a___a____ORNITHINE DECARBOXYLASE. 4.1.1.17__a___a___a___>
       1310          1320          1330          1340          1350
          *       *     *       *     *       *     *       *     *
ATG TGG CAA CTC ATG AAA CAG ATC CAG AGC CAT GGC TTC CCG CCG
Met Trp Gln Leu Met Lys Gln Ile Gln Ser His Gly Phe Pro Pro>
___a___a____ORNITHINE DECARBOXYLASE. 4.1.1.17__a___a___a___>
         1360          1370          1380          1390
          *       *     *       *     *       *     *       *     *
GAG GTG GAG GAG CAG GAT GAT GGC ACG CTG CCC ATG TCT TGT GCC
Glu Val Glu Glu Gln Asp Asp Gly Thr Leu Pro Met Ser Cys Ala>
___a___a____ORNITHINE DECARBOXYLASE. 4.1.1.17__a___a___a___>
       1400          1410          1420          1430          1440
          *       *     *       *     *       *     *       *     *
CAG GAG AGC GGG ATG GAC CGT CAC CCT GCA GCC TGT GCT TCT GCT
Gln Glu Ser Gly Met Asp Arg His Pro Ala Ala Cys Ala Ser Ala>
___a___a____ORNITHINE DECARBOXYLASE. 4.1.1.17__a___a___a___>
         1450          1460          1470          1480
          *       *     *       *     *       *     *       *     *
AGG ATC AAT GTG TAG ATG CCA TTC TTG TAG CTC TTG CCT GCA AGT
Arg Ile Asn Val ***>
___ORNITHINE DE____>
       1490          1500          1510          1520          1530
          *       *     *       *     *       *     *       *     *
TTA GCT TGA ATT AAG GCA TTT GGG GGG ACC ATT TAA CTT ACT GCT
           1540          1550          1560          1570
            *       *     *       *     *       *     *       *
AGT TTG GGA TGT CTT TGT GAG AGT AGG GTT GGC ACC AAT GCA GTA
       1580          1590          1600          1610          1620
          *       *     *       *     *       *     *       *     *
TGG AAG GCT AGG AGA TGG GGG GTC ACA CTT ACT GTG TTC CTA TGG
           1630          1640          1650          1660
            *       *     *       *     *       *     *       *
AAA CTT TGA ATA TTT GTA TTA CAT GGA TTT TTA TTC ACT TTT CAG
       1670          1680          1690          1700          1710
          *       *     *       *     *       *     *       *     *
ACA TTG ATA CTA ACG TGT GCC CCT CAG CTG CTG AGC AAG CGT TTG
           1720          1730          1740
            *       *     *       *     *       *
TAG CTT GTA CAT TGG CAG AAT GGG CCA GAA GC
```

TRANSGENIC MAMMAL ENCODING ORNITHINE DECARBOXYLASE

GOVERNMENT SUPPORT

This invention was made in part with U.S. Government support (National Institutes of Health grants RO1 ES01664 and RO1 CA40402) and the U.S. Government may therefore have certain rights in the invention.

BACKGROUND OF THE INVENTION

The development of transgenic animals has provided important new avenues for the study of specific gene functions in differentiation, embryogenesis and neoplastic development (Palmiter et al., 1986, Ann. Rev. Genet. 20:465–499). Transgenic animals frequently serve as model systems for the study of various disease states and also provide an experimental system in which to test compounds for their ability to regulate disease.

Keratins are a family of polypeptides which constitute the cytoskeleton of intermediate filaments characteristic of epithelial cells. Expression of keratin family members is highly tissue specific and is therefore under stringent regulation. Little is known about the mechanisms controlling the complex tissue specific regulation and inducibility of expression of human keratin 6 (K6) or of the regulation of expression of other keratins (Ramirez et al., 1995, Proc. Natl. Acad. Sci. USA 92:4783–4787).

Ornithine decarboxylase (ODC) catalyzes the decarboxylation of L-ornithine to the diamine putrescine. Putrescine and the polyamines spermidine and spermine are cellular polycations essential for normal cell proliferation and differentiation. ODC expression in mammalian tissues is usually tightly regulated although neoplastic cells often express high levels of the enzyme (Pegg, 1988, Cancer Res. 48:759–774). The deleterious effects of sustained high levels of polyamines on cell proliferation, differentiation, and neoplastic transformation have been studied in situations wherein ODC is constitutively expressed in cells (Hibshoosh et al., 1991, Oncogene 6:739–743). In addition, transgenic mice have been developed which overexpress the human ODC gene in selected tissues such as brain and testis (Halmekyto et al. J. Biol. Chem. 266:19746–19751).

There is a paucity of good experimental animal models for the study of disease states associated with spontaneous tumor formation and abnormal skin, hair and nail growth. The present invention provides such a model by providing a transgenic mammal encoding a chimeric ODC transgene gene which is overexpressed in the epidermis, which overexpression results in abnormal phenotypes including spontaneous tumor development and abnormal skin, hair and nail growth. The transgenic mammal of the invention is useful for the study and development of therapies designed to regulate or ablate such abnormalities.

SUMMARY OF THE INVENTION

The invention features a nonhuman transgenic mammal encoding a chimeric gene. The chimeric gene comprises a keratin promoter/regulatory sequence fused to an ornithine decarboxylase gene, wherein when the chimeric gene is overexpressed in the transgenic mammal, the transgenic mammal exhibits a phenotypic abnormality compared with a nontransgenic littermate.

In one aspect, the nonhuman transgenic mammal of the invention exhibits a phenotypic abnormality which is selected from the group consisting of spontaneous tumor formation, abnormal skin growth, abnormal hair growth and abnormal nail growth.

In another aspect, the nonhuman transgenic mammal of the invention comprises a keratin promoter/regulatory sequence which is selected from the group consisting of K1, K5, K6 and K10 and mammalian homologs thereof. In a preferred embodiment, the keratin promoter/regulatory sequence is K6.

In yet another aspect of the invention, the nonhuman transgenic mammal comprises a keratin promoter/regulatory sequence which has fused to it a nucleotide sequence capable of enhancing expression of the chimeric gene in cells. In a preferred embodiment, the nucleotide sequence is selected from the group consisting of the simian virus 40 early gene enhancer, the cytomegalovirus immediate early gene enhancer and the Rous sarcoma virus enhancer and in another aspect of the invention, the chimeric gene is constitutively expressed.

In even another aspect of the invention, the ornithine decarboxylase gene comprises a mutation which effects premature termination of translation of mRNA transcribed from the ornithine decarboxylase gene thereby rendering ornithine decarboxylase more stable in cells than wild type ornithine decarboxylase. In this embodiment of the invention, the mutation comprises a stop codon at ornithine decarboxylase amino acid position 427.

Preferably, the nonhuman transgenic mammal of the invention is a rodent and more preferably, it is a mouse.

The invention further features a chimeric gene comprising a keratin promoter/regulatory sequence fused to an ornithine decarboxylase gene, wherein when the chimeric gene is overexpressed in a transgenic mammal, the transgenic mammal exhibits a phenotypic abnormality compared with a nontransgenic littermate.

Preferably, the keratin promoter/regulatory sequence is selected from the group consisting of K1, K5, K6 and K10 and mammalian homologs thereof and more preferably, the keratin promoter/regulatory sequence is K6.

In one embodiment of this aspect of the invention, the keratin promoter/regulatory sequence has fused to it a nucleotide sequence capable of enhancing expression of the chimeric gene in cells. Preferably, the nucleotide sequence is selected from the group consisting of the simian virus 40 early gene enhancer, the cytomegalovirus immediate early gene enhancer and the Rous sarcoma virus enhancer. Further, preferably, the chimeric gene of the invention is constitutively expressed.

The chimeric gene of the invention comprises an ornithine decarboxylase gene which comprises a mutation which effects premature termination of translation of mRNA transcribed from the ornithine decarboxylase gene thereby rendering ornithine decarboxylase more stable in cells than wild type ornithine decarboxylase. Preferably, the mutation comprises a stop codon at ornithine decarboxylase amino acid position 427.

The invention further features methods of identifying compounds capable of reducing tumor formation, reducing hair loss, reactivating hair growth in a mammal experiencing hair loss, ameliorating acne or reducing skin wrinkling in a mammal. The method comprises administering to the nonhuman transgenic mammal of the invention a compound suspected of affecting any one or more of the abovementioned phenotypic states and examining the mammal to determine whether the compound affects those phenotypic states.

DESCRIPTION OF THE DRAWINGS

This application contains one color drawing.

FIG. 1 is the DNA sequence of the promoter/regulatory region of the bovine K6 promoter.

FIG. 2 depicts the cDNA sequence of the ornithine decarboxylase gene and the amino acid sequence of the encoded protein. Numbering of amino acids is from the amino terminus to the carboxyl terminus of the protein.

DETAILED DESCRIPTION

Figure 3A:
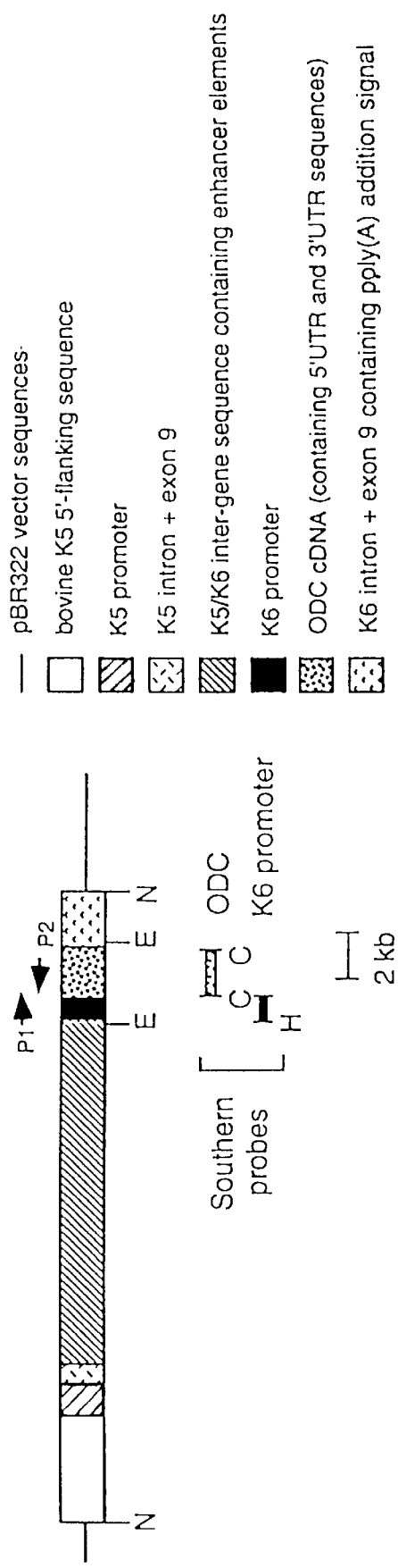
FIG. 3, comprising parts A, B, C, and D, depicts production of transgenic mice which overexpress ODC. A) A diagram of the plasmid construct which was microinjected into mouse embryos. B) Southern blot hybridization analysis of DNA obtained from transgenic and nontransgenic mice. Genomic DNAs obtained from four founder transgenic mice and three nontransgenic littermates were digested with EcoRI and were subjected to Southern blot hybridization analysis. The probe used was a 1.75 kb ODC specific CDNA fragment. Lane 9 contains the plasmid used in the microinjection. The presence of the 2.8 kb band in lanes 2, 4, 5 and 7 is indicative of the presence of the transgene in the founder transgenic mice. C) DNA on the filter shown in (B) was stripped and rehybridized to a probe specific for the K6 promoter. (D) PCR analysis of tail DNA from founder transgenic mice and nontransgenic littermates. Primers derived from the K6 (P1) and ODC cDNA (P2) were used to amplify a 1.2 kb DNA fragment present only in transgenic mice (lanes 4, 5 and 6). Lanes 1, 2 and 3 represent nontransgenic littermates. The same tail DNA was amplified in a separate PCR reaction using primers designed to amplify exon 11 of the endogenous ODC gene (lanes 7–12).

The transgenic mammal of the invention is generated by introducing a chimeric gene into the male pronucleus of a fertilized embryo. The embryo is next implanted into a pseudopregnant mammal of the same species from which the egg was obtained, which mammal then gives birth to the transgenic mammal.

The chimeric gene comprises a promoter/regulatory sequence derived from the keratin family of genes and a coding region comprising ODC. The promoter regulatory sequence may be that which controls expression of K1 (Rothnagel et al., 1990, J. Invest. Derm. 94:573), K5 (Blessing et al., 1993, Genes and Dev. 7:204–215), K6 (Blessing et al., 1987, EMBO J. 6:567–575; Blessing et al., 1989, EMBO J. 8:117–126; Blessing et al., 1995, Teratogenesis, Carcinogenesis and Mutagenesis, 15:11–21) or K10 (Bailleul et al., 1990, Cell 62:697–708) keratin.

The promoter/regulatory sequence comprises a core eukaryotic promoter region and an enhancer region capable of directing tissue specific expression (i.e., expression in epidermis) of any gene fused thereto. Preferably, the basic promoter region comprises from about 300 to about 1000 nucleotides and the enhancer region may comprise any number of additional nucleotides from about 300 to about 30,000 nucleotides depending upon the type of enhancer to be used.

Additional sequence elements may be fused to the promoter/regulatory region which, for example, may facilitate yet further enhanced expression of the gene fused thereto, for example, viral enhancers such as, but not limited to, the simian virus 40 early gene enhancer, the cytomegalovirus immediate early gene enhancer and the Rous sarcoma virus enhancer may be used.

Yet other additional sequence elements which may be fused to the promoter/regulatory sequences include those which facilitate inducible activation of the promoter/regulatory sequence. The invention should therefore be construed to include the addition of inducible sequences to the keratin promoter/regulatory region provided that such addition does not substantially affect tissue specific expression of the transgene. These, as well as other additional sequence elements will be readily apparent to those skilled in the art once armed with the present disclosure.

Preferably, the promoter sequence comprises the K6 promoter sequence having the sequence given in FIG. 1 and all mammalian homologs thereof. Preferably, the "regulatory" (enhancer) sequence positioned 5' to the promoter sequence, is an enhancer sequence conferring tissue specific expression of K6-driven transgene contained within a 11.7 kb SalI-ClaI fragment of the bovine keratin K6 promoter upstream region as described in (Blessing et al., 1990, Genes and Dev. 7:204–215).

By the term "promoter/regulatory sequence" is meant a DNA sequence which is required for tissue-specific expression of a gene fused to the promoter/regulator sequence. In some instances, this sequence may be the core promoter sequence and in other instances, this sequence may also include an enhancer sequence and other regulatory elements which are required for expression of the gene in a tissue-specific manner.

By the term "K6 promoter/regulatory sequence" as used herein is meant a sequence comprising about 605 nucleotides 5' to the transcription initiation site of the bovine cytokeratin IV* (K6) promoter sequence plus an additional about 11,700 nucleotides contiguously 5' to this 605 nucleotide sequence (Blessing et al., 1993, Genes and Dev. 7:204–215).

By the term "K10 promoter/regulatory sequence" as used herein is meant about 5,500 nucleotides 5' to the transcription initiation site of the bovine K10 gene, i.e., the SalI to BamHI fragment of the plasmid pBLCAT3 (Blessing et al., 1989, EMBO J. 8:117–126).

The coding region of the chimeric gene comprises the DNA sequence encoding ODC and any and all mammalian homologs thereof. The ODC gene may comprise the wild type DNA sequence or it may contain a mutation for example, a missense mutation, or any other mutation which results in premature termination of mRNA translation. Premature termination of translation of ODC is engineered within the ODC coding region such that the enzymatic activity of ODC is unaffected; however, the stability of the truncated protein in cells is markedly enhanced compared with wild type protein. By the term "more stable" as it relates to ODC is meant an ODC having a longer halflife in cells than wild type ODC. Although stop codons may be inserted at any one of several amino acid positions at the 3' end of the ODC gene, preferably, premature termination of translation of ODC is effected by positioning a stop codon at ODC amino acid position 427 (Gupta et al., 1985, J. Biol. Chem. 260:2941–2944; Ghoda et al., 1989, Science 243:1493–1495).

Most preferably, the ODC coding region comprises the sequence given in FIG. 2, which sequence, in the chimeric gene, contains a stop codon in the DNA sequence encoding for amino acid 427.

By the term "mammalian homologs thereof", as used herein is meant sequences in mammals which have the same function and which share substantial homology with each other. For example, as described herein, the bovine cytokeratin IV* promoter/regulatory sequences and the human K6 promoter are homologs of each other in that they have the same tissue specific patterns of expression and have substantial sequence homology with each other (Jorcano et al., 1989, J. Mol. Biol. 179:257–281; Jorcano et al., 1984, Differentiation 28:155–162). "Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology.

By way of example, the DNA sequences 3'ATTGCC5' and 3'TATGGC share 50% homology.

By "substantial homology" as used herein refers to a promoter/regulatory sequence which is at least 50% homologous, preferably 60% homologous, more preferably 80% homologous and most preferably 90% homologous to a keratin promoter/regulatory sequence having properties the same or similar to the K6 promoter described herein.

The chimeric gene of the invention may be constitutively expressed in cells or expression of the gene may be inducible. Constitutive or inducible expression is governed by the nature of the sequence elements which are fused to the promoter/regulatory sequence as described above. Inducible elements may include, but are not limited to, sequences comprising the glucocorticoid response element, metal responsive elements, the tetracycline response element and the like, each of which are capable of activating transcription of heterologous genes fused thereto when the respective inducer is present. In addition, overexpression of ODC may also be effected by the addition of yet other enhancer elements to the promoter/regulatory region. Further, overexpression of ODC (i.e., expression to levels higher than that normally found in cells) may be effected by truncation of the carboxyl terminus of the protein which extends the half life of the protein in cells. Thus, additional nucleotide sequences may be added to the keratin promoter/regulatory region, which sequences effect yet further enhanced expression of ODC compared with expression of wild type ODC which is regulated by the native ODC promoter. These additional nucleotide sequences may be derived from any number of sources such as, but not limited to, simian virus 40 early gene enhancer, the cytomegalovirus immediate early gene enhancer and the Rous sarcoma virus enhancer.

The chimeric gene of the invention includes any and all combinations of promoter/regulatory sequences and wild type and truncated forms of ODC which result in the development of phenotypic abnormalities including spontaneous tumor formation and abnormalities in skin, hair and nail growth in transgenic mammals encoding the chimeric gene.

By the term "phenotypic abnormalities" is meant abnormalities which are apparent in transgenic but not in non-transgenic littermates, which abnormalities may be apparent morphologically, i.e., to the naked eye or microscopically, or may be apparent following histochemical, immunocytochemical, immunochemical, biochemical or molecular biological analysis of cells and tissues of the mammal. Transgenic mammals encoding the ODC chimeric gene which exhibit phenotypic abnormalities resulting from the expression of the transgene one or more of these characteristics are included in the invention.

By the term "spontaneous tumor formation" is meant the formation of tumors in the animal at a rate which exceeds the rate of tumor formation in a nontransgenic littermate.

By the term "abnormal skin, hair and nail growth" is meant phenotypic abnormalities (compared with wild type nontransgenic mammals) in the growth of the skin, including, but not limited to excessive wrinkling, acne and the presence of dermal follicular cysts, spontaneous tumor formation and the presence of heavy skin folds; phenotypic abnormalities in the growth of hair including, but not limited to excessive hair loss or alopecia; and, phenotypic abnormalities in nail growth, including but not limited to excessive nail growth. These abnormalities may be apparent morphologically, i.e., to the naked eye or microscopically, or may be apparent following histochemical, immunocytochemical, immunochemical, biochemical or molecular biological analysis of cells and tissues of the mammal. Transgenic mammals encoding the ODC chimeric gene which exhibit one or more of these characteristics are included in the invention.

Introduction of the chimeric gene into the fertilized egg of the mammal is accomplished by any number of standard techniques in transgenic technology (Hogan et al., 1986, Manipulating the Mouse Embryo: A Laboratory Manual, Cold Spring Harbor, N.Y.). Most commonly, the chimeric gene is introduced into the embryo by way of microinjection.

Once the gene is introduced into the egg, the egg is incubated for a short period of time and is then transferred into a pseudopregnant mammal of the same species from which the egg was obtained (Hogan et al., 1986, Manipulating the Mouse Embryo: A Laboratory Manual, Cold Spring Harbor, N.Y.). Typically, 125 eggs are injected per experiment, approximately two-thirds of which will survive the procedure. Twenty viable eggs are transferred into pseudopregnant animals, four to ten of which will develop into live pups. Typically, 10–30% of the pups carry the transgene.

The invention should be construed to include generation of transgenic mammals encoding the chimeric gene, which mammals include mice, hamsters, rats, rabbits, pigs, sheep and cattle. Preferably, the transgenic mammal of the invention is a rodent and most preferably, the transgenic mammal of the invention is a mouse.

To identify the transgenic mammals of the invention, pups are examined for the presence of the chimeric gene using standard technology such as Southern blot hybridization and PCR, described for example, in Sambrook et al., (1989, Molecular Cloning: A Laboratory Manual, Cold Spring Harbor, N.Y.). Expression of the gene in cells and tissues of the mammal is also assessed using ordinary technology. For example, Northern blot hybridization or autoradiographic analyses may be used to detect the presence of chimeric gene specific RNA and Western blot or immunochemical analyses may be used to detect the presence of ODC in cells of the transgenic mammal. Such techniques are common in the art and are described, for example, in Sambrook et al. (supra) and in Harlow et al. (1988, Antibodies, A Laboratory Manual, Cold Spring Harbor, N.Y.).

The effects of ODC expression on growth of the skin, hair and nails are examined morphologically, histochemically, immunochemically, and biochemically using standard technology available in the art. For histochemical analysis, tissues are obtained from the transgenic mammal and are processed for examination by fixation and staining. For immunochemical analysis, an anti-ODC specific antibody is used to detect expression of ODC in the various cells and tissues. While any anti-ODC antibody may be used, the antibody the polyclonal antibody described in Pegg et al. (1983, J. Biol. Chem. 258: 2496–2500) is the preferred antibody.

The transgenic mammal of the invention may be used to identify compounds capable of treating spontaneous tumor formation, and abnormal skin, hair and nail growth in mammals. As described herein in the examples, it is possible to control the onset and severity of skin, hair and nail abnormalities in the transgenic mammals of the invention. Administration of the ornithine analog α-difluoromethylornithine (DFMO) before, during and after the emergence of the phenotypic characteristics of the transgenic mammals serves to regulate such characteristics.

The transgenic mammal of the invention produces an abnormal number of spontaneous skin tumors. Thus, the transgenic mammal provides a means of identifying compounds which are candidate anti-tumor compounds.

To identify anti-tumor compounds, transgenic mammals are administered the compound either before, during or after the development of tumors. Control transgenic mammals are administered a placebo (untreated mammals). The extent of tumor production (i.e., the number and size of the tumors) and/or any regression in the number and size of preexisting tumors is measured in treated versus untreated mammals. A reduction in tumor formation or a regression in growth of preexisting tumors in mammals administered the compound compared with untreated mammals is an indication that the compound is an anti-tumor compound.

Similarly, compounds may be assessed for their ability to affect a reduction in hair loss in mammals. In this case, transgenic mammals are administered the compound either before, during or after the onset of hair loss in the mammal. Control transgenic mammals are administered a placebo (untreated mammals). The extent of reduction in hair loss is assessed in treated versus untreated mammals and a reduction in hair loss in mammals administered the compound compared with untreated mammals is an indication that the compound is effective in reducing hair loss in the mammal.

The transgenic mammals of the invention may also be used to identify compounds for their ability to reactivate hair growth in mammals which have experienced hair loss. In this case, the extent of hair growth in a transgenic mammal administered a compound suspected of affecting hair growth is compared with the extent of hair growth in a transgenic mammal which is not administered the compound. A higher amount of hair growth in the former case compared with the latter case is an indication that the compound is capable of reactivating hair growth. Hair growth and hair loss in mammals may be easily assessed visually using the naked eye, or microscopically.

In an additional use for the transgenic mammals of the invention, compounds capable of ameliorating acne may be identified. Here, the extent of acne in a transgenic mammal administered a compound suspected of ameliorating acne is compared with the extent of acne in a transgenic mammal which is not administered the compound. A lower amount of acne in the former case compared with the latter case is an indication that the compound is capable of ameliorating acne. Measurement of the extent of acne in a mammal may be assessed visually using the naked eye, or microscopically or histologically using the procedures described herein.

In yet another use for the transgenic mammals of the invention, compounds capable of reducing skin wrinkling may be identified. In this case, the extent of skin wrinkling in a transgenic mammal administered a compound suspected of reducing skin wrinkling is compared with the extent of skin wrinkling in a transgenic mammal which is not administered the compound. A lower amount of skin wrinkling in the former case compared with the latter case is an indication that the compound is capable of reducing skin wrinkling. Skin wrinkling may be assessed in a mammal either visually using the naked eye, or microscopically or histologically using the procedures described herein.

In addition, the transgenic mammals may be used to identify compounds which play a role in carcinogenesis and in the prevention thereof.

Compounds to be tested in transgenic mammal for their ability to reduce or ablate the effects of overexpression of ODC may be administered to the mammal in one of the traditional modes (e.g., orally, parenterally, transdermally or transmucosally, intrathecally), in a sustained release formulation using a biodegradable biocompatible polymer, or by on-site delivery using micelles, gels and liposomes, or rectally (e.g., by suppository or enema). The most preferable route of administration is oral administration provided the compound is orally available, by placing the compound in the mammal's drinking water. The compounds can be administered to the mammal in a dosage of 0.1 µg/kg/day to 5 mg/kg/day, either daily or at intervals sufficient to have the desired effects and alleviate the symptoms of the disease. Precise formulations and dosages may be determined using standard techniques, by a pharmacologist of ordinary skill in the art.

The following provides some examples of the present invention. These examples are not to be considered as limiting the scope of the appended claims.

EXAMPLES

A transgenic mouse has been developed wherein expression of a truncated form of ODC has been placed under the control of the K6 promoter/regulatory sequences. Epidermal cells of the transgenic mouse of the invention exhibit constitutive overexpression of truncated ODC resulting in several phenotypic abnormalities such as development of dermal follicular cysts, excessive skin wrinkling, enhanced nail growth, alopecia and spontaneous tumor development.

Overexpression of ODC in epidermis, particularly epidermal keratinocytes, is facilitated by (i) placing the ODC gene under the control of the bovine keratin IV promoter/regulatory region (hereinafter referred to as the K6 promoter/regulatory region) which is homologous to the mouse and human keratin K6 promoter and (ii) by using a form of the ODC gene encoding a premature stop codon such that the carboxyl terminus of the protein is truncated resulting in enhanced stability of the expressed protein in cells (Gupta et al., 1985, J. Biol. Chem. 260:2941–2944; Ghoda et al., 1989, Science 243:1493–1495). Use of the K6 promoter/regulatory region directs expression of genes fused thereto to cells of the outer root sheath of the hair follicle (Blessing et al., 1993, Genes and Dev. 7:204–215).

The data presented herein establish that ODC overexpression targeted to the outer root sheath cells of the hair follicle can profoundly alter skin structure and function. One of the earliest phenotypes observed is disruption of the hair cycle. While the exact time of onset of ODC expression is not yet known, small follicular cysts are present in transgenic skin as early as 2 weeks of age. Because the first hair cycle is normal, it is likely that ODC transgene expression does not become significant until sometime after birth. The hair loss phenotype in these transgenic mice is causally related to ODC overexpression since it can be completely prevented by administration of a specific inhibitor of ODC. While there are numerous mutations in the mouse that cause hair loss (Sundberg (ed), 1994, Handbook of mouse mutations with skin and hair abnormalities, CRC Press, Boca Raton, Fla.), the functions of most of the genes involved are not known. The transgenic mouse of the invention thus provides a mutant mouse strain in which the hair cycle can be experimentally manipulated.

Example 1
Generation of the chimeric gene

A pBR322-based expression vector containing a keratin 5/6 promoter (Blessing et al., 1993, Genes and Dev. 7:204–215) fused to a fragment comprising nucleotides −69 to +1682 of a murine ODC cDNA sequence (Gupta et al., 1985, J. Biol. Chem. 260:2941–2944), which sequence contains a premature stop codon at amino acid position 427 (Ghoda et al., 1989, Science 243:1493–1495) was prepared (FIG. 3A). The cloning procedures for the construction of the K6 promoter/regulatory sequence fused to a truncated ODC gene are standard in the art and are described in the above mentioned references and in Sambrook et al. (1989, Molecular Cloning: A Laboratory Manual, Cold Spring Harbor, N.Y.).

Example 2
Generation of transgenic mice

The plasmid containing the K6 promoter driven transgene was separated from vector sequences by digestion with NotI and the resulting 20 kb fragment was purified by electrophoresis through 1% agarose. The plasmid fragment at a concentration of 1.5 µg/ml was microinjected into the male pronucleus of fertilized B6C3F1 oocytes using standard techniques (Hogan et al., 1986, Manipulating the Mouse Embryo: A Laboratory Manual, Cold Spring Harbor, N.Y.). About 125 eggs were injected. Eggs so injected were incubated for a short period of time and were then transferred into a pseudopregnant mouse (Hogan et al., 1986, Manipulating the Mouse Embryo: A Laboratory Manual, Cold Spring Harbor, N.Y.).

Example 3
Characterization of transgenic mice with respect to the transgene

Figure 3B:
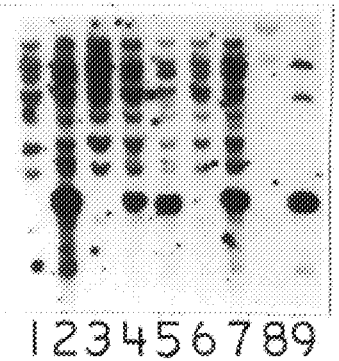
Figure 3C:
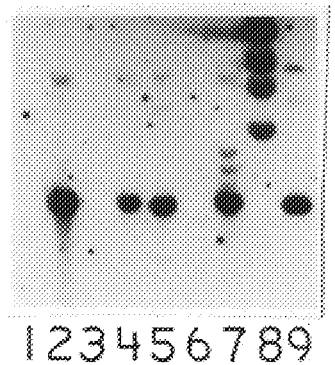

Genomic DNA was isolated from the tails of potential founder mice and was examined by Southern blot hybridization and PCR analysis to identify mice having the transgene. For Southern blot hybridization analysis, DNA was digested with EcoRI and was electrophoresed through 1% agarose gels, transferred to nitrocellulose and was probed sequentially using a 1.75 kb ODC cDNA ClaI fragment and a 4.1 kb BamHI/ClaI DNA fragment derived from the K6 promoter/enhancer region (FIG. 3A and Blessing et al., 1993, Genes and Dev. 7:204–215). Both of the probes were labelled by random primer labelling and hybridized to the same 2.8 kb EcoRI fragment contained in the transgene sequence (FIG. 3B and C).

Figure 3D:
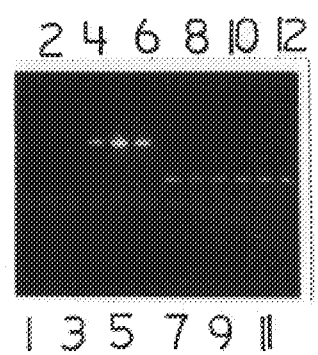

For PCR analysis, the 5' primer, termed P1, contained the following K6 promoter sequence: 5'-GCAGAAGGAGGGGACAATTATCAC-3' (SEQ. ID NO:1). The 3' primer, termed P2, was an oligonucleotide having a sequence corresponding to a portion of the ODC coding region as follows: 5'-TGCCATGTCAAACACACAGCGG-3' (SEQ ID. NO:2). Amplification of the transgene was performed using standard PCR technology, i.e., 30 cycles at 95° C. for 30 minutes, 59° C. for 30 minutes and 72° C. for 1 minute. A 1.2 kb fragment was amplified which spanned the junction between the K6 promoter and the ODC sequences. This fragment was only detected in mice having the transgene (FIG. 3D). Control PCR reactions included the use of two other primers designed to amplify exon 11 of the endogenous ODC gene (5'-GGGGCTATTAAAGAACAATG and 3'[SEQ. ID NO:2] 5'-CCACCACCAAGCAAGCAAAATCA-3" (SEQ. ID NO:4)).

Eight founder mice were identified by PCR analysis of tail DNA, using the above-described primers (FIG. 3D). Southern analysis of tail DNA revealed that multiple copies of the transgene were integrated into genomic DNA in each founder animal (FIG. 3B and C). Quantitative image analysis using a phosphorimager indicated that the transgene copy number varied from 4 to 24 for the various founders analyzed.

Example 4
Phenotypic characterization of transgenic mice

Figure 4:
FIG. 4 is a photograph depicting the appearance of a transgenic mouse.

The appearance of an adult transgenic mouse is shown in FIG. 4. The transgenic mouse exhibits wrinkled skin and heavy skin folds. The nails of the transgenic mouse are also longer. Founder mice were characterized by having a smaller birth weight, a normal first hair cycle followed by progressive hair loss beginning at 2–3 weeks of age, and excessive nail growth (FIG. 4). Hair loss was complete in 6 of 8 founders, but the transgenic progeny of all founders including those with only partial hair loss, exhibited complete hair loss including vibrissae, by 2 months of age. With increasing age the skin of the transgenic mice exhibited pronounced wrinkling and folding and was excessively oily.

For histological analysis, tissues were fixed overnight in 10% neutral buffered formalin or Fekete's solution (60% ethanol, 3.2% formaldehyde, 0.75M acetic acid). The tissues were then embedded in paraffin and 5 µm sections were stained with hematoxylin and eosin. For immunolocalization of ODC, skin sections were incubated with an anti-ODC antiserum and specific staining was detected with an ABC Vectastain kit (Vector Labs, Burlingame, CA) as described (Gilmour et al., 1986, Carcinogenesis 7:943–947).

Figure 5A:
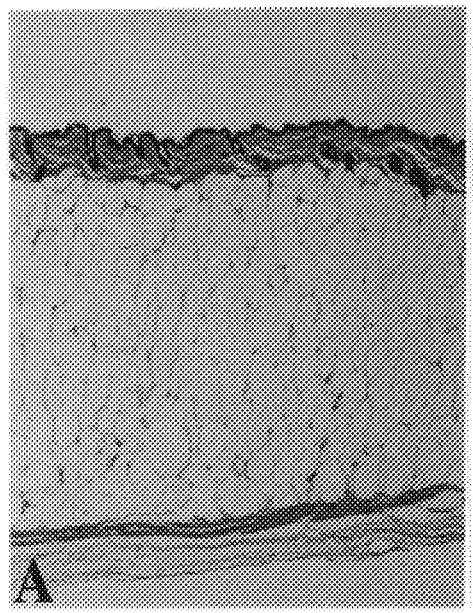
FIG. 5, comprising parts A, B, C and D is a series of photographs depicting histological analysis of the skin of transgenic mice. (A) The skin of a normal mouse at 125× magnification. (B) The skin of a transgenic mouse (at 125× magnification) exhibiting replacement of the subcutaneous fat tissue by large follicular cysts that extend to the muscle layer. (C) A higher power (250× magnification) view of transgenic skin. The cysts vary in size and are lined by well differentiated keratinocytes. (D) Immunohistochemical analysis of transgenic skin depicting expression (brown color) of ODC in the dermis confined to the cell layer lining the cysts. ODC is not overexpressed in the dermis (magnification=250×).
Figure 5B:
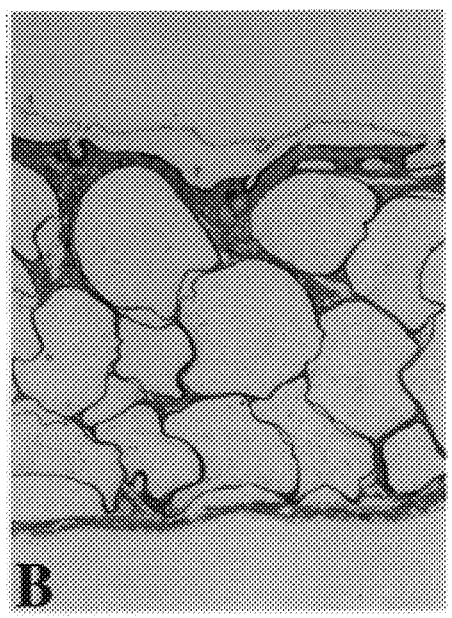
Figure 5C:

Histologic examination revealed that the skin of transgenic mice contained large follicular cysts in the dermis underlying an apparently normal epidermis save for the lack of hair follicles (FIG. 5B). The sebaceous glands adjacent to the follicular cysts were moderately hyperplastic. The cysts in older founders (greater than three months of age) were very large and completely replaced the subcutaneous fat layer. The skin of the transgenic animals also exhibited acne-like lesions, wherein an inflammatory reaction at the base of keratin filled lesions was observed.

Most founders (six out of eight tested) were fertile. The results of breeding experiments indicate that the hair loss phenotype is dominant and the transgene is inherited in a classic Mendelian fashion in that crosses of F1 transgenic mice with normal wild type mice yielded an approximately 1:1 ratio (actually 28:30) of nontransgenic to transgenic pups by PCR analysis.

To analyze transgenic animal tissues biochemically, the mice were killed, the skin was excised and exposed to water at 55° C. for 20 seconds. The epidermis was subsequently scraped off and portions of it were placed either in Buffer A (25 mM Tris-HCl, pH 7.5, 2.5 mM dithiothreitol, 0.1 mM EDTA) or in 0.2N perchloric acid. The remaining dermis was minced thoroughly with scissors and portions were placed in Buffer A or in 0.2N perchloric acid. Tissues so processed were homogenized in a Polytron homogenizer and centrifuged at 20,000×g for 20 minutes. The resulting supernatants were assayed for ODC activity (Buffer A extracts) or for polyamine levels (perchloric acid extracts) as described (Koza et al., 1991, Carcinogenesis 12:1619–1625). Nontransgenic littermates were processed similarly to their transgenic counterparts except that preshaved animals were depilated for 5 minutes immediately after killing. The results of the analysis for ODC are expressed as units/mg protein, wherein 1 unit is equivalent to 1 nmol of $CO_2$ liberated per hour. The results of analysis for the polyamines are expressed as nmols of polyamine/mg DNA.

Figure 5D:
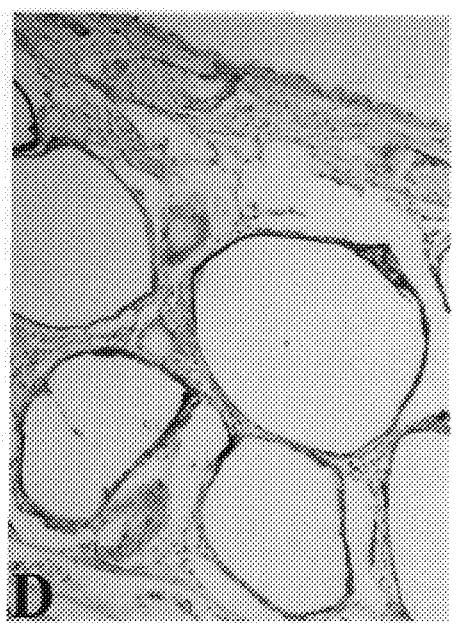

The ODC activity in the skin of transgenic mice was greatly elevated over normal littermates (Table 1). When epidermis and dermis from the same animals were analyzed separately, the increase in ODC activity was found to occur in the dermis rather than the epidermis. The specific activity of ODC in epidermis ranged from 1.4 to 41.3 units/mg protein in various founders, while the specific activity of ODC in the dermis containing follicular cysts was much higher with a range of 33 to 89.8 units/mg. The absolute values of ODC activity in transgenic dermis were much higher than previously reported for induced levels of this enzyme in epidermis (O'Brien et al., 1975, Cancer Res. 35:1662–1670; Weeks et al., 1982, Proc. Natl. Acad. Sci. USA 79:6028–6032). Immunocytochemical analysis revealed high levels of ODC expression in small, flattened keratinocytes lining the dermal follicular cysts. Immunocytochemical analysis was performed as described by Gilmour et al. (1986, Carcinogenesis 7:943–947) except that the antibody dilution was 1:3000. There was no detectable overexpression of ODC in the epidermis using this method of analysis (FIG. 5D).

TABLE 1

Ornithine Decarboxylase Levels in Transgenic Mouse Skin

| Mouse | Age (mos) | Sex | ODC Specific Activity units/mg protein in: | |
|---|---|---|---|---|
| | | | Epidermis | Dermis |
| Founder 1 | 5 | F | 24.1 | ND |
| Littermates (n = 3) | 5 | F | 0.05 ± 0.01 | ND |
| Founder 2A | 3.75 | M | 1.36 | ND |
| Founder 2B | 5.40 | M | 8.60 | 89.8 |
| Littermates (n = 2) | 3.75 | M/F | 0.14 | ND |
| Founder 3 | 4.4 | F | 41.3 | 85.10 |
| Littermate | 4.4 | F | 0.5 | 0.06 |
| Founder 4 | 6.5 | F | 7.1 | 79.10 |
| Littermate | 6.5 | F | 0.06 | |
| Founder 5 | 10.5 | M | 12.3 | 45.3 |
| Littermate | 10.5 | M | 0.01 | 0.08 |
| Founder 6A | 9.3 | M | 5.4 | 62.1 |
| Founder 6B | 10.2 | F | 12.9 | 33.0 |
| Littermate | 9.3 | M | 0.55 | 0.03 |

Polyamine levels were determined as described in Koza et al., 1991, Carcinogenesis 12:1619–1625.

Figure 6:
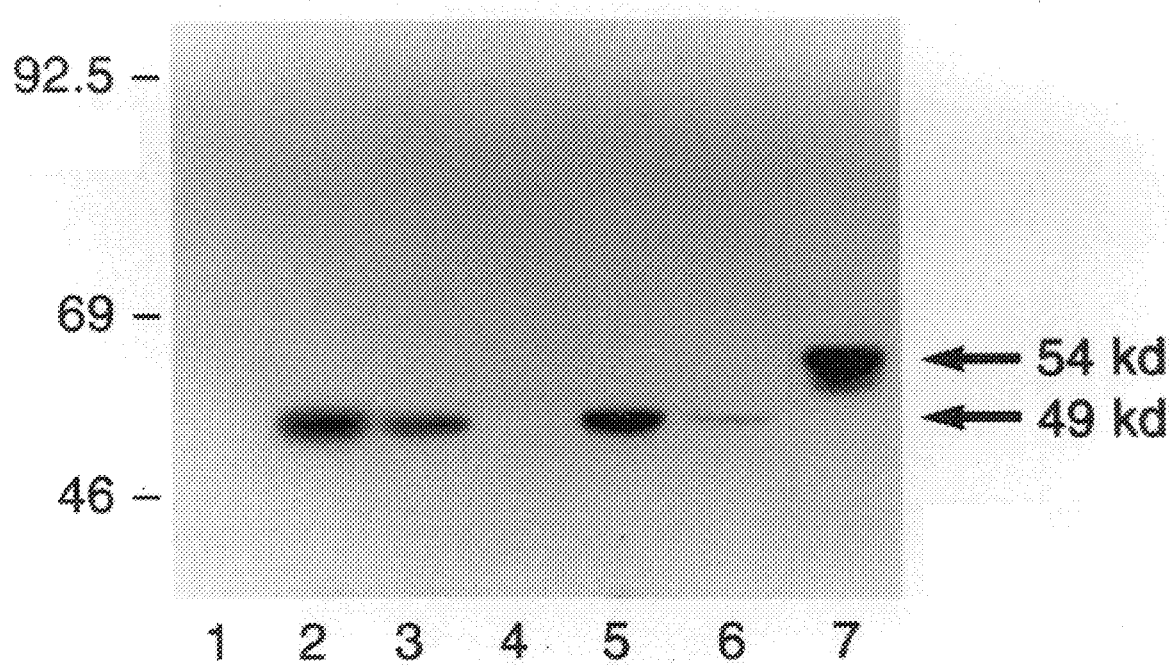
FIG. 6 is a photograph depicting Western blot analysis of ODC expression in transgenic and nontransgenic mice. Crude extracts of protein obtained from epidermis (lane 6) or dermis (lanes 2, 3 and 5) of founder transgenic mice or from dermis of nontransgenic littermates (lanes 1 and 4) were electrophoresed through a 10% SDS polyacrylamide gel. The proteins were transferred to nitrocellulose and were incubated in the presence of an ODC-specific antibody at a 1:20,000 dilution (Pegg, 1983, J. Biol. Chem. 258:2496–2500). A protein extract obtained from testosterone-induced mouse kidney served as a positive control (lane 7). The insertion of the premature stop codon into the ODC gene results in a protein which is smaller (by 5 kD) than the endogenous ODC protein.

To confirm that the elevated ODC expression was the result of expression of the transgene, Western blot analysis was performed (FIG. 6). The only protein which was detected by this method in extracts of transgenic epidermis or dermis was approximately 49 kD, the predicted size of the truncated ODC transgene product. No expression of the endogenous gene product (~54 kD) was detected in either normal or transgenic epidermis or dermis.

Polyamine levels, particularly putrescine and spermidine, were greatly elevated in transgenic mouse dermis compared to nontransgenic littermates. The levels of putrescine and spermidine were also elevated in epidermis relative to levels in control littermate tissues, but not to the same extent as in dermis (Table 2). For example, in founder #4, putrescine was elevated 37-fold over normal litter-mate values in dermis, but only a 4-fold elevation was evident in epidermis.

TABLE 2

Polyamine Levels in Normal vs Tranegenic Skin

| | Polyamine nmol/mg DNA in: | | | | | |
|---|---|---|---|---|---|---|
| | Epidermis | | | Dermis | | |
| Mouse | Pu | Spd | Sp | Pu | Spd | Sp |
| Founder 2A | 77.9 | 349 | 171 | N.D | N.D. | N.D. |
| Littermates (n = 2) | 66.2 | 228 | 224 | | | |
| Founder 4 | 179 | 645 | 179 | 839 | 1220 | 154 |
| Littermate | 44.7 | 478 | 306 | 22.5 | 365 | 285 |
| Founder 5 | 176 | 356 | 137 | 382 | 448 | 98.7 |
| Littermate | 103 | 760 | 728 | 11.3 | 162 | 133 |
| Founder 6A | 359 | 720 | 302 | 1248 | 1297 | 217 |

TABLE 2-continued

Polyamine Levels in Normal vs Tranegenic Skin

| | Polyamine nmol/mg DNA in: | | | | | |
|---|---|---|---|---|---|---|
| | Epidermis | | | Dermis | | |
| Mouse | Pu | Spd | Sp | Pu | Spd | Sp |
| Founder 6B | 134 | 443 | 217 | 371 | 645 | 178 |
| Littermate | 80.6 | 346 | 398 | 16.3 | 248 | 157 |

Polyamine levels were determined as described in Koza et al., 1991, Carcinogenesis 12: 1619–1625.

Example 5
The effect of an ODC inhibitor on the development of phenotypic abnormalities The ornithine analog DFMO, an enzyme-activated irreversible inhibitor of ODC (Metcalf et al., 1978, J. Amer. Chem. Soc. 100:2551–2553), was used to determine whether inhibition of transgene expression could prevent the development of any of the observed phenotypic abnormalities in the transgenic mice. A male founder was mated with a nontransgenic mouse and a litter of 13 pups was obtained. Seven pups encoded the transgene by PCR analysis. DFMO (at 1% weight/volume) was administered in the drinking water to the nursing female beginning 1 day after birth. At weaning, all pups appeared normal in all respects. Three of the transgenic pups were then given normal drinking water while four of the transgenic pups were given water containing DFMO. After 6 weeks, at the approximate time of the beginning of the third hair cycle, mice which were administered normal drinking water began to exhibit hair loss. Mice which remained on drinking water containing DFMO appeared to have normal hair coats. Histologic examination revealed that transgenic mice administered DFMO had a normal skin morphology while mice which had not been administered DFMO for up to 12 weeks exhibited the characteristic dermal follicular cysts seen in founder transgenic animals, although the cysts were smaller and less abundant than in the founder mice. In addition, ODC and putrescine levels in the latter mice (those which had not been administered DFMO for up to 12 weeks) were significantly elevated in the dermis compared to mice which were administered DFMO. In over one hundred matings of transgenic mice with normal wild type B6C3F1 mice, all of the transgenic progeny exhibited hair loss by weaning at 3 weeks of age and complete hair loss by 8 weeks of age.

Example 6
Tumor formation in transgenic mice

Figure 7A:
FIG. 7, comprising parts A–F, is a series of photographs depicting histochemical analysis of spontaneous tumors in transgenic mice. Many of the observed lesions are keratoacanthoma-like, characterized by dome-shaped endophytic lesions with moderately differentiated keratinocytes and a central area filed with keratin (k) from the mouth (A), the tail (B and E) and the ear (C). Bone tissue (b) and skeletal muscle can be seen in panel B. A detail of a squamous lesion from the dorsal skin with more aggressive cytological features is shown in panel (D). In panel (F) there is illustrated immunolocalization of ODC in the tumor shown in panel (E). The tumor was fixed overnight in Fekete's solution and subsequently embedded in paraffin. Sections were cut and incubated with anti-ODC antibody at a dilution of 1:500.
Figure 7B:
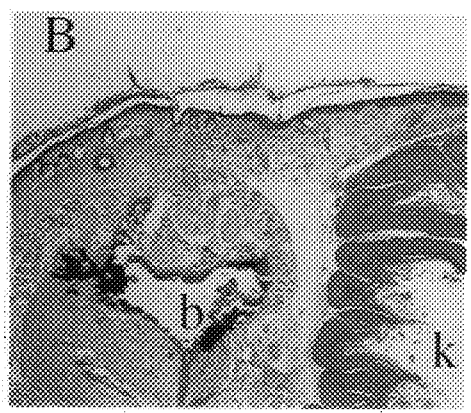
Figure 7C:
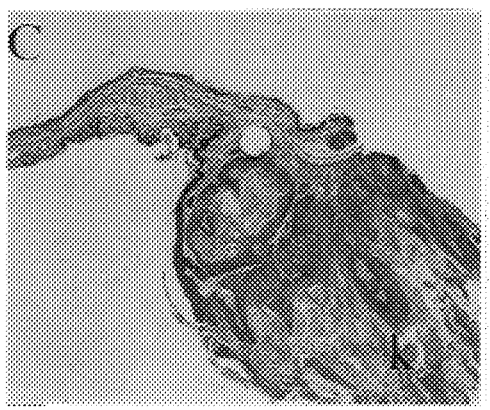
Figure 7D:
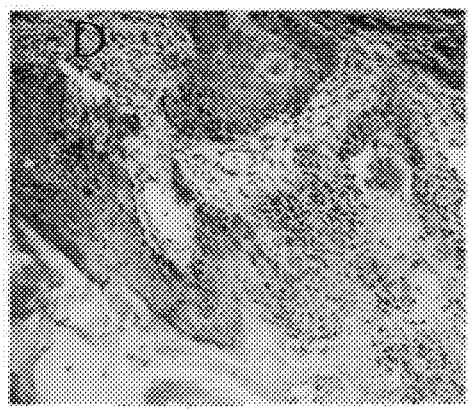
Figure 7E:
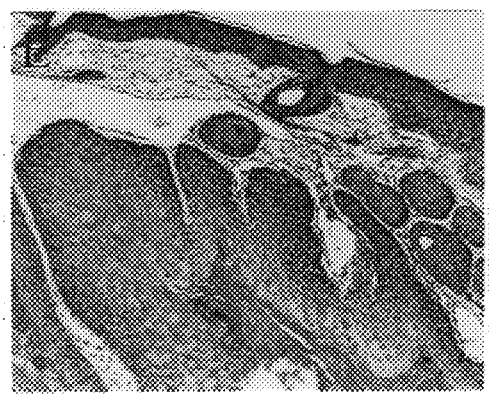
Figure 7F:
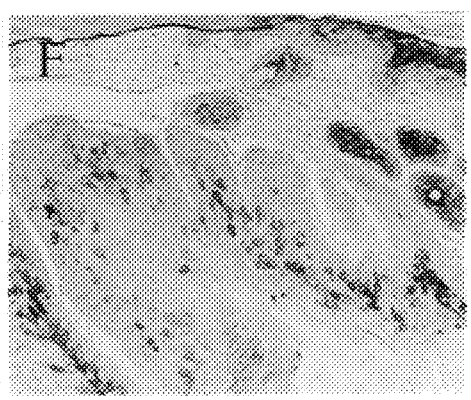

Transgenic mice developed spontaneous skin tumors at a high frequency. For example, three out of eight founder animals developed at least one grossly visible skin lesion. The F1 progeny of founders also developed skin tumors at a similar frequency to that of the founders (approximately 40%), while nontransgenic littermates never exhibited tumor formation. Each of the skin lesions were squamous neoplasms having varying degrees of dysplasia and aggressive character. Histological examination of five of the tumors is shown in FIG. 7. Keratoacanthoma-like lesions were common (FIG. 7A–C), while well differentiated papillomatous lesions were also observed (FIG. 7D and E). Tumors were frequently found on the tail, face and ears as well as the dorsal and ventral skin. Squamous cell carcinomas were not observed.

The results of an analysis of ODC activity in the tumors are presented in Table 3. The absolute values of ODC specific activity were extremely high in all tumors. When the tumor illustrated in FIG. 7E was analyzed for ODC expression immunocytochemically, intense staining was observed throughout the tumor, particularly in the suprabasal cells. Western blot analysis for ODC expression in this tumor revealed that ODC overexpression was the result of expression of the transgene rather than by activation of the endogenous wild type ODC gene.

TABLE 3

ODC Activity in Spontaneous Skin Tumors Arising In Transgenic Mice

| Tumor | Mouse | ODC Sp. Act. |
|---|---|---|
| A1 | Founder | 36.4 |
| B1 | F1 | 120 |
| C1 | F1 | 103 |
| D1 | F1 | 113 |
| E1 | F1 | 33.0 |
| F1 | F1 | 146 |
| G1 | Founder | 34.0 |

Mean ± S.E.M. = 83.6 ± 18.0

The disclosures of each and every patent, patent application and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype selected from the group consisting of alopecia, spontaneous growth of squamous neoplasms, substantial skin folding or wrinkling, excessive nail growth, oily skin and follicular cysts in the skin.

2. The transgenic mouse of claim 1, wherein said keratin promoter/regulatory sequence is selected from the group consisting of the K1 promoter/regulatory sequence, the K6 promoter/regulatory sequence, the K6 promoter/regulatory sequence, the K10 promoter/regulatory sequence, and mammalian homologs thereof.

3. The transgenic mouse of claim 2, wherein said keratin promoter/regulatory sequence is the K6 promoter/regulatory sequence.

4. The transgenic mouse of claim 1, wherein said chimeric DNA sequence further comprises a nucleotide sequence which enhances expression of said ornithine decarboxylase in cells.

5. The transgenic mouse of claim 4, wherein said nucleotide sequence is selected from the group consisting of the simian virus 40 early gene enhancer, the cytomegalovirus immediate early gene enhancer and the Rous sarcoma virus enhancer.

6. The transgenic mouse of claim 1, wherein said chimeric DNA sequence is constitutively expressed.

7. The transgenic mouse of claim 1, wherein said sequence encoding an ornithine decarboxylase comprises a mutation which effects premature termination of translation of mRMA transcribed from said sequence encoding an ornithine decarboxylase thereby rendering said ornithine decarboxylase more stable in cells than wild type ornithine decarboxylase.

8. The transgenic mouse of claim 7, wherein said mutation comprises a stop codon at ornithine decarboxylase amino acid position 427.

9. The transgenic mouse of claim 1, wherein the specific activity of ornithine decarboxylase in the dermal tissue of said transgenic mouse is at least about fifty times greater than the specific activity of ornithine decarboxylase in the dermal tissue of a non-transgenic littermate.

10. The transgenic mouse of claim 1, wherein the specific activity of ornithine decarboxylase in the epidermal tissue of said transgenic mouse is at least about five times greater than the specific activity of ornithine decarboxylase in the epidermal tissue of a non-transgenic littermate.

11. A chimeric DNA sequence comprising a keratin promoter/regulatory sequence operably linked to a sequence encoding an ornithine decarboxylase, wherein, upon introduction into the somatic and germ cells of a mouse, the expression of said ornithine decarboxylase in the epidermis or dermis of said mouse results in a phenotype selected from the group consisting of alopecia, spontaneous growth of squamous neoplasms, substantial skin folding or wrinkling, excessive nail growth, oily skin and follicular cysts in the skin.

12. The chimeric DNA sequence of claim 11, wherein said keratin promoter/regulatory sequence is selected from the group consisting of the K1 promoter/regulatory sequence, the K5 promoter/regulatory sequence, the K6 promoter/regulatory sequence, the K10 promoter/regulatory sequence, and mammalian homologs thereof.

13. The chimeric DNA sequence of claim 12, wherein said keratin promoter/regulatory sequence is the K6 promoter/regulatory sequence.

14. The chimeric DNA sequence of claim 11 which further comprises a nucleotide sequence which enhances expression of said ornithine decarboxylase in cells.

15. The chimeric DNA sequence of claim 11, wherein said nucleotide sequence is selected from the group consisting of the simian virus 40 early gene enhancer, the cytomegalovirus immediate early gene enhancer and the Rous sarcoma virus enhancer.

16. The chimeric DNA sequence of claim 11, wherein said chimeric DNA is constitutively expressed.

17. The chimeric DNA sequence of claim 11, wherein said sequence encoding an ornithine decarboxylase comprises a mutation which effects premature termination of translation of mMRA transcribed from said sequence encoding an ornithine decarboxylase thereby rendering said ornithine decarboxylase more stable in cells than wild type ornithine decarboxylase.

18. The chimeric DNA sequence of claim 17, wherein said mutation comprises a stop codon at ornithine decarboxylase amino acid position 427.

19. A method of identifying a compound capable of reducing hair loss in a mammal comprising:
   a) generating a transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype selected from the group consisting of alopecia, spontaneous growth of squamous neoplasms, substantial skin folding or wring, longer tan normal nail growth, oily skin and follicular cysts in the skin;
   b) administering said compound to said transgenic mouse; and
   c) comparing the amount of hair loss in the transgenic mouse of step (b) with the amount of hair loss in a nontreated transgenic littermate, wherein a lower amount of hair loss in said treated transgenic mouse is an indication that said compound is capable of reducing hair loss in said mammal.

20. A method of identifying a compound capable of reactivating hair growth in a mammal experiencing hair loss, said method comprising:
   a) generating a transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype of alopecia;
   b) administering said compound to said transgenic mouse; and
   c) comparing the amount of hair growth in the transgenic mouse of step (b), with the amount of hair growth in a nontreated transgenic littermate, wherein a higher amount of hair growth in said treated transgenic mouse is an indication that said compound is capable of reactivating hair growth in said mammal.

21. A method of identifying a compound capable of ameliorating follicular cysts in a mammal comprising:
   a) generating a transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype of follicular cysts in the skin;
   b) administering said compound to said transgenic mouse; and
   c) comparing the amount of follicular cysts in the transgenic mouse of step (h), with the amount of follicular cysts in a nontreated transgenic littermate, wherein a lower amount of follicular cysts in said treated transgenic mouse is an indication that said compound is capable of ameliorating follicular cysts in said mammal.

22. A method of identifying a compound capable of reducing the amount of oil in the skin of a mammal, comprising:
   a) generating a transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype of ;oily skin
   b) administering said compound to said transgenic mouse; and
   c) comparing the amount of oil in the skin of the transgenic mouse of step (b), with the amount of oil in the skin of a nontreated transgenic littermate, wherein a reduced amount of oil in the skin of said treated transgenic mouse is an indication that said compound is capable of reducing the amount of oil in the skin of said mammal.

23. A method of identifying a compound capable of reducing skin wrinkling in a mammal, comprising:
   a) generating a transgenic mouse whose somatic and germ cells contain a chimeric DNA sequence comprising a keratin promoter/regulatory sequence operably linked to a sequence encoding an ornithine decarboxylase, wherein the expression of said ornithine decarboxylase in the epidermis or dermis of said mouse results in a phenotype of substantial skin folding or wrinkling;
   b) administering said compound to said transgenic mouse; and
   c) comparing the amount of skin wrinkling in the transgenic mouse of step (b), with the amount of skin wrinkling in a nontreated transgenic littermate, wherein a lower amount of hair growth in said treated transgenic mouse is an indication that said compound is capable of reducing skin wrinkling in said mammal.

* * * * *

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GCAGAAGGAG GGGACAATTA TCAC 24

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

TGCCATGTCA AACACACAGC GG 22

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GGGGCTATTA AAGAACAATG 20

( 2 ) INFORMATION FOR SEQ ID NO:4:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

CCACCACCAA GCAAGCAAAA TCA 23

( 2 ) INFORMATION FOR SEQ ID NO:5:

( i ) SEQUENCE CHARACTERISTICS:
        ( A ) LENGTH: 630 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO (iv) ANTI-SENSE: NO (xi) SEQUENCE DESCRIPTION: SEQ ID NO:5:

| | | | | | | |
|---|---|---|---|---|---|---|
| AAGCTTGTTC | TTATGCTGTA | AAAACTCATC | TCCTTTGTCC | CTCTTGCCTT | TCAAAGGAGT | 60 |
| GTCATGTCCC | CAGAGTAGCC | CCCAATTCCC | AGGCCAGGCC | ACCAGGAAGG | CAGTCAGGAG | 120 |
| ATCCAGAAGG | ACATGTTCAA | ACATGGCCCA | AAACCACCGC | AAGCCACTTT | CTTGCTCAGA | 180 |
| CCACAGGCAA | ATGCCTATTA | ACCCTCAGAG | ACGTTCAACC | TGAATGGGAA | GGGTGGTGTG | 240 |
| AGTGGAGAAG | AAAACTTGTG | TGGGAAGGGG | GCAAGAGAAG | AGTGTCTGAG | TAAGCAGAAG | 300 |
| GAGGGGACAA | TTATCACAGA | TCAGCTCCTT | GTCTCCTTTG | TTTGAGAGCA | TGACTAACCC | 360 |
| ATGACTTCAG | TGAATTTACA | TCCAGTGGTA | TTGTGTTGGG | ATCAAGTCAA | GGCTAGAAGC | 420 |
| CAGAAGAATT | TCTCCATGAC | TAAAGGAAAC | CAAAGAAGCA | ATATTCATAC | TTCATACCTT | 480 |
| TCTAGAGGCA | GGGGGTGATC | TCACTATTTG | TAAAGCCCAG | CCCTTTCTAA | TCTGCAGGCT | 540 |
| CACCTTCCAG | GACTGAGCCC | GGCCCATTTT | TTCCATATAT | AAGCTGCTGC | CGGGCCGCCC | 600 |
| TCTATAGATC | TGGATCTCGA | CGGTATCGAT | | | | 630 |

(2) INFORMATION FOR SEQ ID NO:6:

(i) SEQUENCE CHARACTERISTICS:
        (A) LENGTH: 1742 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

| | | | | | | |
|---|---|---|---|---|---|---|
| GTCGACCTTG | TGAGGAGCTG | GTGATAATTT | GATTCCATCT | CCAGGTTCCC | TGTAAGCACA | 60 |
| TCGAGAACCA | TGAGCAGCTT | TACTAAGGAC | GAGTTTGACT | GCCACATCCT | TGATGAAGGC | 120 |
| TTTACTGCTA | AGGACATTCT | GGACCAAAAA | ATCAATGAAG | TCTCTTCCTC | TGACGATAAG | 180 |
| GATGCGTTCT | ATGTTGCGGA | CCTCGGAGAC | ATTCTAAAGA | AGCATCTGAG | GTGGCTAAAA | 240 |
| GCTCTTCCCC | GCGTCACTCC | CTTTTACGCA | GTCAAGTGTA | ACGATAGCAG | AGCCATAGTG | 300 |
| AGCACCCTAG | CTGCCATTGG | GACAGGATTT | GACTGTGCAA | GCAAGACTGA | AATACAGTTG | 360 |
| GTGCAGGGGC | TTGGGGTGCC | TGCAGAGAGG | GTTATCTATG | CAAATCCTTG | TAAGCAAGTC | 420 |
| TCTCAAATCA | AGTATGCTGC | CAGTAACGGA | GTCCAGATGA | TGACTTTTGA | CAGTGAAATT | 480 |
| GAATTGATGA | AAGTCGCCAG | AGCACATCCA | AAGGCAAAGT | TGGTTCTACG | GATTGCCACT | 540 |
| GATGATTCCA | AAGCTGTCTG | TCGCCTCAGT | GTTAAGTTTG | GTGCCACACT | CAAAACCAGC | 600 |
| AGGCTTCTCT | TGGAACGGGC | AAAAGAGCTA | AATATTGACG | TCATTGGTGT | GAGCTTCCAT | 660 |
| GTGGGCAGTG | GATGTACTGA | TCCTGATACC | TTCGTTCAGG | CAGTGTCGGA | TGCCCGCTGT | 720 |
| GTGTTTGACA | TGGCAACAGA | AGTTGGTTTC | AGCATGCATC | TGCTTGATAT | TGGTGGTGGC | 780 |
| TTTCCTGGAT | CTGAAGATAC | AAAGCTTAAA | TTTGAAGAGA | TCACCAGTGT | AATCAACCCA | 840 |
| GCTCTGGACA | AGTACTTCCC | ATCAGACTCT | GGAGTGAGAA | TCATAGCTGA | GCCAGGCAGA | 900 |
| TACTATGTCG | CATCAGCTTT | CACGCTTGCA | GTCAACATCA | TTGCCAAAAA | AACCGTGTGG | 960 |
| AAGGAGCAGC | CCGGCTCTGA | CGATGAAGAT | GAGTCAAATG | AACAAACCTT | CATGTATTAT | 1020 |
| GTGAATGATG | GAGTATATGG | ATCATTTAAC | TGCATTCTTT | ATGATCATGC | CCATGTGAAG | 1080 |
| GCCCTGCTGC | AGAAGAGACC | CAAGCCAGAC | GAGAAGTATT | ACTCATCCAG | CATCTGGGGA | 1140 |

-continued

```
CCAACATGTG ATGGCCTTGA TCGGATCGTG GAGCGCTGTA ACCTGCCTGA AATGCATGTG     1200

GGTGATTGGA TGCTGTTTGA GAACATGGGT GCATACACCG TTGCTGCTGC TTCTACTTTC     1260

AATGGGTTCC AGAGGCCAAA CATCTACTAT GTAATGTCAC GGCCAATGTG CAACTCATG      1320

AAACAGATCC AGAGCCATGG CTTCCCGCCG GAGGTGGAGG AGCAGGATGA TGGCACGCTG     1380

CCCATGTCTT GTGCCCAGGA GAGCGGGATG GACCGTCACC CTGCAGCCTG TGCTTCTGCT     1440

AGGATCAATG TGTAGATGCC ATTCTTGTAG CTCTTGCCTG CAAGTTTAGC TTGAATTAAG     1500

GCATTTGGGG GGACCATTTA ACTTACTGCT AGTTTGGGAT GTCTTTGTGA GAGTAGGGTT     1560

GGCACCAATG CAGTATGGAA GGCTAGGAGA TGGGGGGTCA CACTTACTGT GTTCCTATGG     1620

AAACTTTGAA TATTTGTATT ACATGGATTT TTATTCACTT TTCAGACATT GATACTAACG     1680

TGTGCCCCTC AGCTGCTGAG CAAGCGTTTG TAGCTTGTAC ATTGGCAGAA TGGGCCAGAA     1740

GC                                                                    1742
```

( 2 ) INFORMATION FOR SEQ ID NO:7:

( i ) SEQUENCE CHARACTERISTICS:
        ( A ) LENGTH: 461 amino acids
        ( B ) TYPE: amino acid
        ( C ) STRANDEDNESS: single
        ( D ) TOPOLOGY: linear ( i i ) MOLECULE TYPE:
        ( A ) DESCRIPTION: /desc = "protein"

( i i i ) HYPOTHETICAL: NO ( i v ) ANTI-SENSE: NO ( x i ) SEQUENCE DESCRIPTION: SEQ ID NO:7:

```
Met Ser Ser Phe Thr Lys Asp Glu Phe Asp Cys His Ile Leu Asp Glu
  1               5                  10                  15

Gly Phe Thr Ala Lys Asp Ile Leu Asp Gln Lys Ile Asn Glu Val Ser
             20                  25                  30

Ser Ser Asp Asp Lys Asp Ala Phe Tyr Val Ala Asp Leu Gly Asp Ile
         35                  40                  45

Leu Lys Lys His Leu Arg Trp Leu Lys Ala Leu Pro Arg Val Thr Pro
     50                  55                  60

Phe Tyr Ala Val Lys Cys Asn Asp Ser Arg Ala Ile Val Ser Thr Leu
 65                  70                  75                  80

Ala Ala Ile Gly Thr Gly Phe Asp Cys Ala Ser Lys Thr Glu Ile Gln
                 85                  90                  95

Leu Val Gln Gly Leu Gly Val Pro Ala Glu Arg Val Ile Tyr Ala Asn
            100                 105                 110

Pro Cys Lys Gln Val Ser Gln Ile Lys Tyr Ala Ala Ser Asn Gly Val
        115                 120                 125

Gln Met Met Thr Phe Asp Ser Glu Ile Glu Leu Met Lys Val Ala Arg
    130                 135                 140

Ala His Pro Lys Ala Lys Leu Val Leu Arg Ile Ala Thr Asp Asp Ser
145                 150                 155                 160

Lys Ala Val Cys Arg Leu Ser Val Lys Phe Gly Ala Thr Leu Lys Thr
                165                 170                 175

Ser Arg Leu Leu Leu Glu Arg Ala Lys Glu Leu Asn Ile Asp Val Ile
            180                 185                 190

Gly Val Ser Phe His Val Gly Ser Gly Cys Thr Asp Pro Asp Thr Phe
        195                 200                 205
```

| | | | | | | | | | | | | | | |
|---|---|---|---|---|---|---|---|---|---|---|---|---|---|---|
| Val | Gln | Ala | Val | Ser | Asp | Ala | Arg | Cys | Val | Phe | Asp | Met | Ala | Thr | Glu |
| | 210 | | | | | 215 | | | | | 220 | | | | |
| Val | Gly | Phe | Ser | Met | His | Leu | Leu | Asp | Ile | Gly | Gly | Gly | Phe | Pro | Gly |
| 225 | | | | | 230 | | | | | 235 | | | | | 240 |
| Ser | Glu | Asp | Thr | Lys | Leu | Lys | Phe | Glu | Glu | Ile | Thr | Ser | Val | Ile | Asn |
| | | | | 245 | | | | | 250 | | | | | 255 | |
| Pro | Ala | Leu | Asp | Lys | Tyr | Phe | Pro | Ser | Asp | Ser | Gly | Val | Arg | Ile | Ile |
| | | | 260 | | | | | 265 | | | | | 270 | | |
| Ala | Glu | Pro | Gly | Arg | Tyr | Tyr | Val | Ala | Ser | Ala | Phe | Thr | Leu | Ala | Val |
| | | 275 | | | | | 280 | | | | | 285 | | | |
| Asn | Ile | Ile | Ala | Lys | Lys | Thr | Val | Trp | Lys | Glu | Gln | Pro | Gly | Ser | Asp |
| | 290 | | | | | 295 | | | | | 300 | | | | |
| Asp | Glu | Asp | Glu | Ser | Asn | Glu | Gln | Thr | Phe | Met | Tyr | Tyr | Val | Asn | Asp |
| 305 | | | | | 310 | | | | | 315 | | | | | 320 |
| Gly | Val | Tyr | Gly | Ser | Phe | Asn | Cys | Ile | Leu | Tyr | Asp | His | Ala | His | Val |
| | | | | 325 | | | | | 330 | | | | | 335 | |
| Lys | Ala | Leu | Leu | Gln | Lys | Arg | Pro | Lys | Pro | Asp | Glu | Lys | Tyr | Tyr | Ser |
| | | | 340 | | | | | 345 | | | | | 350 | | |
| Ser | Ser | Ile | Trp | Gly | Pro | Thr | Cys | Asp | Gly | Leu | Asp | Arg | Ile | Val | Glu |
| | | 355 | | | | | 360 | | | | | 365 | | | |
| Arg | Cys | Asn | Leu | Pro | Glu | Met | His | Val | Gly | Asp | Trp | Met | Leu | Phe | Glu |
| | 370 | | | | | 375 | | | | | 380 | | | | |
| Asn | Met | Gly | Ala | Tyr | Thr | Val | Ala | Ala | Ala | Ser | Thr | Phe | Asn | Gly | Phe |
| 385 | | | | | 390 | | | | | 395 | | | | | 400 |
| Gln | Arg | Pro | Asn | Ile | Tyr | Tyr | Val | Met | Ser | Arg | Pro | Met | Trp | Gln | Leu |
| | | | | 405 | | | | | 410 | | | | | 415 | |
| Met | Lys | Gln | Ile | Gln | Ser | His | Gly | Phe | Pro | Pro | Glu | Val | Glu | Glu | Gln |
| | | | 420 | | | | | 425 | | | | | 430 | | |
| Asp | Asp | Gly | Thr | Leu | Pro | Met | Ser | Cys | Ala | Gln | Glu | Ser | Gly | Met | Asp |
| | | 435 | | | | | 440 | | | | | 445 | | | |
| Arg | His | Pro | Ala | Ala | Cys | Ala | Ser | Ala | Arg | Ile | Asn | Val | | | |
| | 450 | | | | | 455 | | | | | 460 | | | | |